| United States Patent [19] | [11] | 4,350,699 |
|---|---|---|
| Fahmy et al. | [45] | Sep. 21, 1982 |

[54] PYRIDYLALKOXYSULFINYL DERIVATIVES OF CARBAMATE ESTERS

[75] Inventors: Mohamed A. H. Fahmy, Princeton, N.J.; Tetsuo R. Fukuto, Riverside, Calif.; Teruomi Jojima, Sagamihara, Japan

[73] Assignee: The Regents of the University of California, Los Angeles, Calif.

[21] Appl. No.: 248,820

[22] Filed: Mar. 30, 1981

[51] Int. Cl.³ .................. C07D 213/54; C07D 213/55; C07D 213/56; A01N 43/40

[52] U.S. Cl. .................................... 424/263; 546/336; 546/331; 546/330; 546/334; 546/335; 546/337

[58] Field of Search ............... 546/336, 331, 330, 334, 546/335, 337; 424/263

[56] References Cited

U.S. PATENT DOCUMENTS

| 4,156,780 | 5/1979 | Kilbourn et al. | 546/330 |
| 4,233,289 | 11/1980 | Kilbourn et al. | 546/330 |
| 4,298,617 | 11/1981 | Fahmy et al. | 424/298 |

*Primary Examiner*—John M. Ford
*Attorney, Agent, or Firm*—Albert M. Herzig; Edward C. Walsh; Max Geldin

[57] ABSTRACT

A novel class of chemical compounds useful as pesticides consists of pyridylalkoxysulfinyl derivatives of carbamate esters. The preparation of these compounds and their formulation to control insects are exemplified.

34 Claims, No Drawings

PYRIDYLALKOXYSULFINYL DERIVATIVES OF CARBAMATE ESTERS

BACKGROUND OF THE INVENTION

This invention relates to the general field of pesticides, and is particularly concerned with the production of insecticides for the control of both household insects and crop insects.

U.S. Pat. No. 3,997,549 to Fukuto and Black discloses N-arylsulfenylated derivatives of benzofuranyl methylcarbamates as effective pesticides.

U.S. Pat. No. 4,006,231 to Black and Fukuto discloses N-aminosulfenylated derivatives of carbonfuran as effective pesticides.

U.S. Pat. No. 3,843,689 to Brown discloses production of N-methyl or N-phenyldithiocarbamates produced from N-chlorothiocarbamates, as insecticides.

In the copending application Ser. No. 18,598, filed Mar. 7, 1979, by M. A. H. Fahmy and T. R. Fukuto, a novel class of chemical compounds useful as pesticides, consisting of N-alkoxy- and N-aryloxy sulfinylcarbamate esters, and their method of preparation are described.

In the copending application, Ser. No. 18,417, filed Mar. 7, 1979, by M. A. H. Fahmy and T. R. Fukuto, now U.S. Pat. No. 4,262,015, a novel class of chemical compounds useful as pesticides, consisting of N-alkylthio- and N-arylthiosulfinylcarbamate esters, and their method of preparation are disclosed.

The object of the present invention is to provide another novel class of carbamate ester compounds which are effective pesticides, and procedure for preparing same.

SUMMARY OF THE INVENTION

The novel carbamate ester compounds of the invention are generally pyridylalkoxysulfinyl derivatives of carbamate esters. The compounds are prepared by reacting an N-chlorosulfinylcarbamate ester with a pyridine alkanol, in a suitable organic solvent such as tetrahydrofuran in the presence of a hydrogen chloride acceptor such as pyridine.

The resulting compounds of the invention are highly effective against certain pests and insects, and have substantially reduced mammalian toxicity, e.g. as compared to other potent insecticides such as the compound $(CH_3)(CH_3S)C=N-O-CO-NHCH_3$, known as methomyl. Thus, the invention compounds, while having high toxicity toward certain insect pests, are relatively safe to mammals.

DETAILED DESCRIPTION OF THE INVENTION AND PREFERRED EMBODIMENTS

The sulfinyl carbamate esters of the invention have the formula noted below.

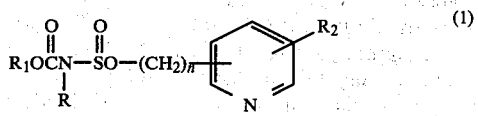

wherein R is methyl; $R_1$ is selected from the class consisting of a hydrocarbyl group containing from 1 to 20 carbon atoms, and the $>C=N-$ group; $R_2$ is selected from the class consisting of hydrogen, a lower alkyl group containing from 1 to 4 carbon atoms, and a halogen atom; and n is an integer of from 1 to 5.

Thus, $R_1$ can be a hydrocarbyl group containing only hydrogen and carbon, and from 1 to 20 carbon atoms, preferably 1 to 12 carbon atoms, either aliphatic or aromatic, including substituted or unsubstituted alkyl, cycloalkyl, phenylalkyl and naphthylalkyl; and substituted or unsubstituted aryl, such as phenyl and naphthyl; and wherein the aforementioned groups can be substituted with one or more halogen, cyano, nitro, alkyl, alkylthio, dialkylamino and alkoxy groups; or $R_1$ can be the $>C=N-$ group which can be represented more specifically by the formula:

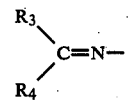

where $R_3$ is hydrogen, alkyl, alkylthio or cyano, and $R_4$ is alkyl, alkylthio, alkoxy, alkanoyl, alkoxycarbonyl, dialkylaminocarbonyl or phenyl, all of which can be unsubstituted or substituted with one or more cyano, nitro, alkylthio, alkylsulfinyl, alkylsulfonyl or alkoxy groups.

Where $R_1$ is aryl, preferred examples of such aryl groups are as follows:

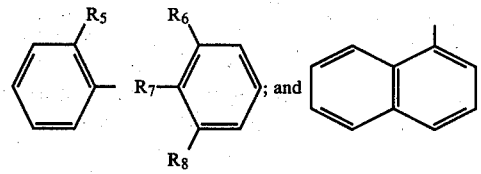

where $R_5$ is hydrogen, alkoxy, alkylthio, alkyl, alkylthioalkyl, 2-dioxolanyl or halogen, e.g. Cl or Br;

$R_6$ is alkyl, alkoxy, alkoxyalkyl or halogen;

$R_7$ is hydrogen, alkyl, halogen, alkylthio, alkoxy, dialkylamino or formyl(alkyl)amino;

$R_8$ is hydrogen or alkyl; and wherein the number of aliphatic carbon atoms in $R_3$, $R_4$, $R_5$, $R_6$, $R_7$, and $R_8$, individually should not exceed eight:

In one group of preferred carbamate ester compounds of the invention, $R_1$ is a hydrocarbyl group containing from 1 to 12 carbon atoms, either aliphatic or aromatic, including alkyl, e.g. methyl, ethyl, isopropyl, propyl, isobutyl, cycloalkyl, e.g. cyclohexyl, phenylalkyl, naphthylalkyl; aryl, e.g. phenyl, naphthyl, alkylphenyl, e.g. tolyl, xylyl, alkylnaphthyl, any of which can contain substituents such as halogen, e.g. chlorine or bromine, alkoxy, alkylthio and dialkylamino. Particularly preferred are those compounds where $R_1$ is alkyl, phenyl, and naphthyl groups, and which can be unsubstituted or substituted, e.g. with halogen, alkoxy, dialkylamino, alkylthio groups, and the like, and especially wherein $R_1$ is alkylaryl, e.g. a 3-alkylphenyl such as 3-methylphenyl, 3-isopropylphenyl, and 3-sec-butylphenyl, 2-alkoxyphenyl such as 2-isopropoxyphenyl, dialkylaminophenyl such as 3-methyl-4-dimethylamino and 3,5-dimethyl-4-dimethylaminophenyl, or 1-naphthyl.

Another particularly preferred class of carbamates of the invention are those wherein $R_1$ is a group containing the >C=N— radical, as defined above. Such >C=N— groups can be, for example, the following:

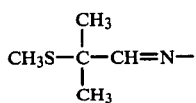  (2)

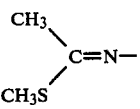  (3)

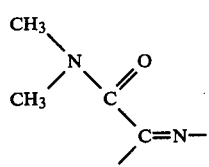  (4)

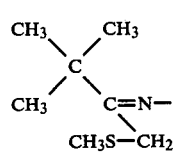  (5)

R$_2$ in all of the above preferred compounds can be a hydrogen atom; a lower alkyl group as defined above, such as methyl, ethyl, propyl, isopropyl, n-butyl, and sec-butyl; or a halogen atom such as fluorine, chlorine, bromine and iodine. Where R$_2$ is a lower alkyl group, e.g. methyl, there can be more than one R$_2$ group, e.g. 1 to 3 such R$_2$ groups, on the pyridine ring.

The carbamate esters of the invention can be prepared by the following general reaction scheme:

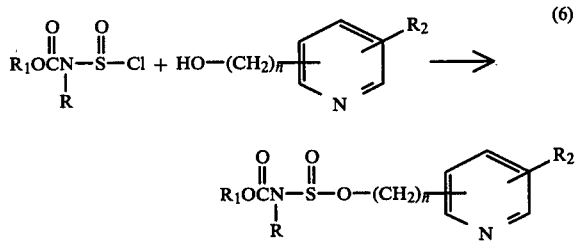  (6)

wherein R, R$_1$, R$_2$ and n are defined above.

In the above reaction, the N-chlorosulfinylcarbamate ester intermediate is formed by the reaction of the corresponding carbamate with thionyl chloride, preferably using pyridine as hydrogen chloride acceptor in an inactive polar solvent such as tetrahydrofuran. However, other HCl acceptors such as triethylamine also can be used. Non-polar solvents such as hexane also can be used. Such ester can be formed in high yield using essentially equivalent quantities of the carbamate and thionyl chloride and slightly more than an equivalent amount of HCl acceptor such as pyridine. These novel intermediates and their method of production are described in the co-pending application Ser. No. 18,416, filed Mar. 7, 1979, by M. A. H. Fahmy and T. R. Fukuto.

Without isolation, the N-chlorosulfinylcarbamate ester intermediates can react in situ with pyridine alkanols in the presence of an equivalent amount of pyridine or triethylamine as hydrogen chloride acceptor to form pyridylalkoxysulfinyl derivatives of carbamate esters. In general, the reaction can be carried out at temperatures ranging from about 10° to about 60° C., e.g. ambient temperature, in an organic solvent such as dichloromethane, benzene, dimethylformamide, hexane or tetrahydrofuran.

It will be understood that if desired, the N-chlorosulfinylcarbamate ester starting material in reaction (6) above can be initially prepared and isolated as an intermediate compound, and such compound then reacted with the appropriate pyridine alkanols, as noted in the above reaction scheme.

The following examples are representative of the preparation of the invention compounds.

EXAMPLE I

Synthesis of S-methyl N-[N'-methyl-N'-(2-pyridylmethoxy)-sulfinylcarbamoyloxy] thioacetimidate (I)

To a cold solution of S-methyl N-(methylcarbamoyloxy) thioacetimidate (1.62 g, 0.01 mol) and pyridine (0.988 g, 0.0125 mol) in 10 ml dry tetrahydrofuran was added 1.25 g of freshly distilled thionyl chloride and the mixture was stirred for 5 hours at room temperature. The reaction mixture was cooled to 5° C., and pyridine (0.988 g) and 2-pyridine-methanol (1.09 g, 0.01 mol) were added successively to it.

After the reaction mixture was stirred for 1 hour at room temperature, it was diluted with 70 ml of ether. The mixture was washed with cold water twice (10 ml each). The ether was dried over anhydrous magnesium sulfate and evaporated under vacuum to give 2.65 g (84%) of crude product as a yellow crystalline solid. Recrystallization of such product from hexane-ethyl acetate (3:1) gave 1.59 g of pure material as colorless needles, m.p. 65°–66° C.

Anal. calcd. for $C_{11}H_{15}N_3O_4S_2$: C, 41.63%; H, 4.76%. Found: C, 41.28%; H, 4.39%.

EXAMPLE II

Synthesis of 3-methylphenyl N-[1-(2'-pyridyl)-2-ethoxysulfinyl]-N-methylcarbamate (II)

A solution of 3-methylphenyl N-chlorosulfinyl-N-methylcarbamate prepared from 3-methylphenyl methylcarbamate (1.65 g, 0.01 mol), pyridine (0.988 g), thionyl chloride (1.25 g) and anhydrous tetrahydrofuran (10 ml) as described in Example I was cooled to 5° C. To this solution, 0.988 g pyridine and 1.23 g 2-pyridinethanol was added successively. The reaction mixture was stirred for 1 hour while the temperature was allowed to rise to ambient. Dichloromethane (70 ml) was added to the mixture and the solution was washed twice with cold water. The organic layer was dried over anhydrous magnesium sulfate and concentrated in vacuo to give 3.1 g (93%) of crude product as a yellow oil. The starting material, 3-methylphenyl emthylcarbamate (0.3 g) was precipitated out by adding hexane to the oil. A portion of the above oil was further purified by silica gel preparative TLC (thin-layer chromatography) using benzene-ethyl acetate (4:1) as the developing solvent, $n_D^{24}$ 1.5500.

Anal. calcd. for $C_{16}H_{18}N_2O_4S$: C, 57.47%; H, 5.43%. Found: C, 58.25%; H, 5.75%.

The following are additional examples of the carbamate esters of the invention:

III S-methyl N-[N'-methyl-N'-(3-pyridylmethoxy)sulfinylcarbamoyloxy]-thioacetimidate. m.p. 85°–87°

IV S-methyl N-{N'-methyl-N'-[1-(2-pyridyl)-2-ethoxy]-sulfinylcarbamoyloxy}thioacetimidate. $n_D^{24}$ 1.5523

V S-methyl N-{N'-methyl-N'-[1-(3-pyridyl)-3propoxy]-sulfinylcarbamoyloxy}thioacetimidate. $n_D^{24}$ 1.5250

VI 3-Methylphenyl N-(2-pyridylmethoxysulfinyl)-N-methylcarbamate. $n_D^{24}$ 1.5560

VII 3-Methylphenyl N-(4-pyridylmethoxysulfinyl)-N-methylcarbamate. $n_D^{24}$ 1.5505

VIII 3-Methylphenyl N-[1-(3-pyridyl)-3-propoxysulfinyl]-methylcarbamate. $n_D^{24}$ 1.5498

IX 3-Isopropylphenyl N-(2-pyridylmethoxysulfinyl)-N-methylcarbamate. $n_D^{24}$ 1.5430

X 3-Isopropylphenyl N-[1-(2-pyridyl)-2-ethoxysulfinyl]-N-methylcarbamate. $n_D^{24}$ 1.5440

XI 3-Isopropylphenyl N-[1-(3-pyridyl)-3-propoxysulfinyl]-N-methylcarbamate. $n_D^{24}$ 1.5420

XII 3-Isopropylphenyl N-[3-(4-methylpyridyl)methoxysulfinyl]-N-methyl carbamate.

XIII 3-Methyephenyl N-[3-(6-chloropyridyl)methoxysulfinyl]-N-methyl carbamate.

The insecticidal pyridylalkoxysulfinyl derivatives of carbamate esters of the invention may be formulated with the usual carriers, including additives and extenders used in the preparation of insecticidal compositions. Thus, the toxicants of this invention, like most insecticidal agents, are generally not applied full strength, but are incorporated with the adjuvants and carriers normally employed for facilitating the dispersion of active ingredients, recognizing the accepted fact that the formulation and mode of application of a toxicant may affect the activity of the material.

The present compounds may be made into liquid concentrates by solution or emulsification in suitable liquids such as organic solvents, and into solid concentrates by admixing with talc, clays, and other known solid carriers used in the insecticide art. These concentrates are compositions containing about 5–50% toxicant and the rest inert material which includes dispersing agents, emulsifying agents and wetting agents. The concentrates are diluted for practical application with water or other liquid sprays or with additional solid carrier for application as a dust or granular formulation.

The concentration of the toxicant in the dilution generally used for application is normally in the range of about 2% to 0.001%. Many variations of spraying and dusting compositions in the art may be used, by substituting a compound of this invention into compositions known or apparent to the art.

Insecticidal compositions may be formulated and applied with other active ingredients, including other insecticides, nematocides, acaricides, fungicides, plant regulators, fertilizers, etc. In applying chemicals, it is obvious that an effective amount and concentration of the carbamate ester compounds of the invention should be employed.

BIOLOGICAL ACTIVITY

Representative compounds of the pyridylalkoxysulfinyl derivatives of carbamate esters of the invention were tested for insecticidal activity against house flies and tobacco cutworms, and for mammalian toxicity against mice.

In the test for houseflies, stock 1% concentrated solutions of each of the test compounds and the commercially related carbamate ester insecticide, methomyl, were made in acetone, and such solutions were diluted with acetone to a concentration of 0.001–0.1%. House flies were treated topically on the notum by 1 μl of each of the diluted acetone solutions and percent mortality was counted 24 hours after application. Insects were held at a constant temperature of 60° F. Results are presented as $LD_{50}$ in μg/g.

In the test against tobacco cutworms, aqueous solutions containing each toxicant at 100 and 500 ppm and an emulsifying agent, Shingramin, at 0.03% were prepared. The composition of Shingramin is understood to consist of 20% of polyoxyethylene dodecyl ether and polyoxyethylene alkylaryl ether, 12% ligninsulfonates and 68% inert solvents, by weight. A cabbage leaf was dipped into each of these solutions for 30 seconds, and put in a paper cup of 8 cm diameter. Ten tobacco cutworms (3rd instar larvae) were released onto the leaf. Two leaves were used for each dilution. Mortality of the insects was counted 72 hours after the treatment.

Mammalian toxicity was determined against Swiss white mice. The test compound was applied orally using propylene glycol as the carrier. Results are given as $LD_{50}$ in mg of compound per kg body weight. The toxicological data for typical esters of the invention are summarized in Table I.

The term "$LD_{50}$" represents the dose needed to kill 50% of the test animals. Interpreting the values in the Table below, the lower the value of $LD_{50}$ for house flies, the greater the insecticidal potency or toxicity of that particular compound. On the other hand, the higher the value of $LD_{50}$ for mice, the lower the mammalian toxicity or the greater is the mammalian safety of such compound.

TABLE I

Toxicity of the Carbamate Esters of the Invention Against House Flies, Tobacco Cutworms and White Mice

| Compound | House Flies $LD_{50}$ (μg/g) | Tobacco Cutworms mortality (%) at 500 ppm | Tobacco Cutworms mortality (%) at 100 ppm | Mice $LD_{50}$ (mg/kg) |
|---|---|---|---|---|
| 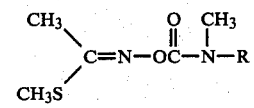 | | | | |
| R = | | | | |
| 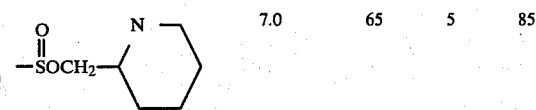 (I) | 7.0 | 65 | 5 | 85 |
| 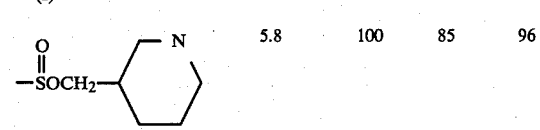 (III) | 5.8 | 100 | 85 | 96 |
| H (methomyl) | 3.7 | 100 | 100 | 10 |
| 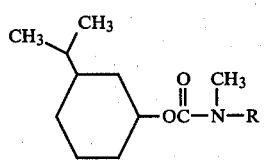 | | | | |
| R = | | | | |

TABLE I-continued

Toxicity of the Carbamate Esters of the Invention Against House Flies, Tobacco Cutworms and White Mice

| Compound | House Flies LD$_{50}$ (μg/g) | Tobacco Cutworms mortality (%) at 500 ppm | 100 ppm | Mice LD$_{50}$ (mg/kg) |
|---|---|---|---|---|
| 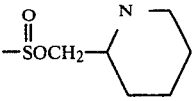 (IX) | 111.5 | | | 105 |
| H (MIP) | 41.0 | | | 16 |

The relatively low values for the compounds, I, III, and IX of the invention listed in Table I for LD$_{50}$ for house flies indicates good toxicity of the invention compounds as against such insects, although I was not as potent as methomyl for tobacco cutworms. However, and of particular significance, the mammalian toxicity of the invention compounds, I and III, as indicated by their high LD$_{50}$ values of 85 and 96, respectively, for mice, is low as compared with the much higher toxicity as indicated by an LD$_{50}$ value of 10 for the parent carbamate, methomyl. Also, the invention compound IX has a substantially lower mammalian toxicity as indicated by its LD$_{50}$ value, 105, as contrasted to the much higher mammalian toxicity of the parent carbamate ester MIP, as indicated by its LD$_{50}$ value of 16. Thus, the above table shows that the carbamate esters of the invention have good insecticidal activity or potency, but have substantially reduced mammalian toxicity or substantially greater mammalian safety.

While we have described particular embodiments of the invention for purposes of illustration, it will be understood that various changes and modifications within the spirit of the invention can be made, and the invention is not to be taken as limited except by the scope of the appended claims.

What is claimed is:

1. A carbamate ester having pesticidal activity selected from the group represented by the formula:

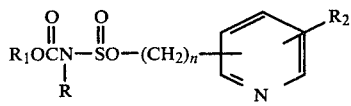

wherein R is methyl; R$_1$ is selected from the class consisting of a hydrocarbyl group containing from 1 to 20 carbon atoms, and a group containing the >C=N— radical; R$_2$ is selected from the class consisting of hydrogen; a lower alkyl group containing from 1 to 4 carbon atoms, and a halogen atom, and n is an integer of from 1 to 5.

2. A carbamate as defined in claim 1, wherein R$_1$ is the group:

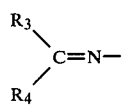

where

R$_3$ is hydrogen, alkyl, alkylthio or cyano, and
R$_4$ is alkyl, alkylthio, alkoxy, alkanoyl, alkoxycarbonyl, dialkylaminocarbonyl, or phenyl, which can be unsubstituted or substituted with cyano, nitro, alkylthio, alkylsulfinyl, alkylsulfonyl or alkoxy groups, the number of aliphatic carbon atoms in R$_3$ and R$_4$ not exceeding eight.

3. A carbamate as defined in claim 1, wherein R$_1$ is an aryl group selected from the class consisting of:

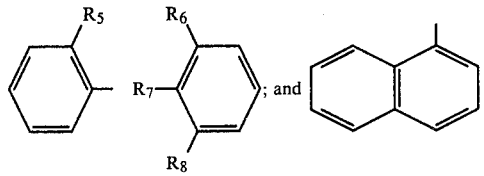

where R$_5$ is hydrogen, alkoxy, alkylthio, alkyl, alkylthioalkyl, 2-dioxolanyl, or halogen;
R$_6$ is alkyl, alkoxy, alkoxyalkyl, or halogen;
R$_7$ is hydrogen, alkyl, halogen, alkylthio, alkoxy, dialkylamino or formyl(alkyl)amino; and
R$_8$ is hydrogen or alkyl; the number of aliphatic carbon atoms in R$_5$, R$_6$, R$_7$, and R$_8$, individually, not exceeding eight.

4. A carbamate as defined in claim 3, wherein R$_1$ is:

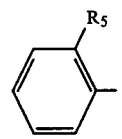

5. A carbamate as defined in claim 3, wherein R$_1$ is:

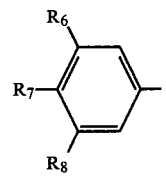

6. A carbamate as defined in claim 1, wherein R$_1$ is 1-naphthyl.

7. Carbamates as defined in claim 1, wherein R$_2$ is hydrogen.

8. A carbamate as defined in claim 1, wherein R$_2$ is a lower alkyl group containing from 1 to 4 carbon atoms, and there are 1 to 3 said alkyl groups on the pyridine ring.

9. A carbamate as defined in claim 7, wherein n is 1 and the —(CH$_2$)$_n$— group is attached to the 2- or 3-position of the pyridine ring.

10. A carbamate as defined in claim 1, where R$_1$ is a hydrocarbyl group containing from 1 to 12 carbon atoms.

11. A carbamate as defined in claim 1, wherein R$_1$ is an aryl group selected from the group consisting of phenyl and naphthyl.

12. A carbamate as defined in claim 11, wherein said aryl group can be substituted with one or more halogen, cyano, nitro, alkyl, alkylthio, dialkylamino, and alkoxy groups.

13. A carbamate as defined in claim 11, wherein R$_1$ is selected from the group consisting of 3-methylphenyl, 3-isopropylphenyl, 3-sec-butylphenyl, 2-isopropoxyphenyl, 3-methyl-4-dimethylaminophenyl, and 3,5-dimethyl-4-dimethylaminophenyl.

14. A carbamate as defined in claim 1, wherein $R_1$ is selected from the class having the formulae:

$$CH_3S-\underset{\underset{CH_3}{|}}{\overset{\overset{CH_3}{|}}{C}}-CH=N-$$

$$\underset{CH_3}{\overset{CH_3}{\diagdown}}N\underset{C}{\overset{O}{\diagup}}\diagdown C=N-$$
$$\quad\quad CH_3S$$

$$\underset{CH_3S}{\overset{CH_3}{\diagdown}}C=N-; \text{ and}$$

$$\underset{CH_3}{\overset{CH_3}{\diagdown}}\underset{\underset{CH_3S-CH_2}{|}}{C}\diagdown C=N-$$
$$\quad\quad\quad CH_3$$

15. A carbamate as defined in claim 1, wherein $R_1$ is the group $$\underset{CH_3S}{\overset{CH_3}{\diagdown}}C=N-$$

and R is methyl.

16. A carbamate as defined in claim 1, wherein $R_1$ is alkylaryl and R is methyl.

17. A carbamate as defined in claim 15, wherein n is 1 and the $-(CH_2)_n-$ group is attached to the 2- or 3-position of the pyridine ring.

18. A carbamate as defined in claim 16, wherein n is 1 and the $-(CH_2)_n-$ group is attached to the 2- or 3-position of the pyridine ring.

19. Carbamate as defined in claim 1, which is S-methyl N-[N'-methyl-N'-(2-pyridylmethoxy)sulfinylcarbamoyloxy]thioacetimidate.

20. Carbamate as defined in claim 1, which is 3-methylphenyl N-[1-(2'-pyridyl)-2-ethoxysulfinyl]-N-methylcarbamate.

21. Carbamate as defined in claim 1, which is S-methyl N-[N'-methyl-N'-(3-pyridylmethoxy)sulfinylcarbamoyloxy]thioacetimidate.

22. Carbamate as defined in claim 1, which is S-methyl N-{N'-methyl-N'-[1-(2-pyridyl)-2-ethoxy]sulfinylcarbamoyloxy}thioacetimidate.

23. Carbamate as defined in claim 1, which is 3-isopropylphenyl N-(2-pyridylmethoxysulfinyl)-N-methylcarbamate.

24. An insecticidal composition comprising an insecticidally effective amount of a carbamate as defined in claim 1, in admixture with a carrier.

25. An insecticidal composition comprising as insecticidally effective amount of a carbamate as defined in claim 3, in admixture with a carrier.

26. An insecticidal composition comprising an insecticidally effective amount of a carbamate as defined in claim 13, in admixture with a carrier.

27. An insecticidal composition comprising an insecticidally effective amount of a carbamate as defined in claim 14, in admixture with a carrier.

28. The method of controlling insects which comprises applying to the sites of infestation an insecticidally effective amount of a compound as defined in claim 1.

29. The method of controlling insects which comprises applying to the sites of infestation an insecticidally effective amount of a compound as defined in claim 13.

30. The method of controlling insects which comprises applying to the sites of infestation an insecticidally effective amount of a compound as defined in claim 15.

31. The method of controlling insects which comprises applying to the sites of infestation an insecticidally effective amount of a compound as defined in claim 21.

32. A method for the preparation of a carbamate ester selected from the group represented by the formula:

$$R_1O\overset{O}{\overset{\|}{C}}\underset{\underset{R}{|}}{N}-\overset{O}{\overset{\|}{S}}O-(CH_2)_n-\underset{N}{\diagup\diagdown}^{R_2}$$

which comprises reacting a compound of the formula $$R_1O\overset{O}{\overset{\|}{C}}\underset{\underset{R}{|}}{N}-\overset{O}{\overset{\|}{S}}-Cl$$

with a compound having the formula $$HO-(CH_2)_n-\underset{N}{\diagup\diagdown}^{R_2}$$

wherein R is methyl; $R_1$ is selected from the class consisting of a hydrocarbyl group containing from 1 to 20 carbon atoms, and a group containing the $>C=N-$ radical; $R_2$ is selected from the class consisting of hydrogen, a lower alkyl group containing from 1 to 4 carbon atoms, and a halogen atom; and n is an integer of from 1 to 5.

33. The method as defined in claim 32, the reaction taking place in the presence of a hydrogen chloride acceptor and at temperature ranging from about 10° to about 60° C.

34. The method as defined in claim 33, the reaction being carried out in an organic solvent.

* * * * *